United States Patent
Dosho

(10) Patent No.: US 6,748,048 B2
(45) Date of Patent: Jun. 8, 2004

(54) ATTACHMENT OF X-RAY APPARATUS, HIGH TEMPERATURE ATTACHMENT AND X-RAY APPARATUS

(75) Inventor: Akihide Dosho, Tokyo (JP)

(73) Assignee: Rigaku Corporation, Akishima (JP)

( * ) Notice: Subject to any disclaimer, the term of this patent is extended or adjusted under 35 U.S.C. 154(b) by 44 days.

(21) Appl. No.: 10/295,867

(22) Filed: Nov. 18, 2002

(65) Prior Publication Data

US 2003/0095634 A1 May 22, 2003

(30) Foreign Application Priority Data

Nov. 16, 2001 (JP) ........................................ 2001-351094

(51) Int. Cl.⁷ .............................................. G01N 23/20
(52) U.S. Cl. ............................. 378/79; 378/80; 378/81
(58) Field of Search ............................. 378/79, 80, 81, 378/86, 70, 75, 71, 147, 154

(56) References Cited

U.S. PATENT DOCUMENTS

| | | | | |
|---|---|---|---|---|
| 4,147,618 A | * | 4/1979 | Richardson et al. | 378/89 |
| 4,169,228 A | * | 9/1979 | Briska et al. | 378/45 |
| 4,263,510 A | * | 4/1981 | Ciccarelli et al. | 378/46 |
| 4,506,375 A | * | 3/1985 | Manson | 378/207 |
| 5,390,230 A | * | 2/1995 | Chang | 378/80 |
| 6,359,964 B1 | * | 3/2002 | Kogan | 378/87 |
| 6,418,190 B1 | * | 7/2002 | Yokozawa et al. | 378/81 |

* cited by examiner

Primary Examiner—Craig E. Church
Assistant Examiner—Irakli Kiknadze
(74) Attorney, Agent, or Firm—Burns, Doane, Swecker & Mathis, L.L.P.

(57) ABSTRACT

An attachment 3 mounted on a specimen support portion 2 of an X-ray apparatus 1 includes a cover member 9 covering a specimen S and a scattered ray excluding member 8 provided between the cover member 9 and the specimen S. The scattered ray excluding member 8 takes in the form of a box, a case or enclosure defined by a wall 16. The enclosure has a large opening 14a on the side of the cover member 9 and a small opening 14b on the side of the specimen S. The scattered ray excluding member 8 functions to prevent scattered X-ray emitted from the cover member when X-rays from an X-ray source passes through the cover member 9 and traveling toward an X-ray detector.

24 Claims, 4 Drawing Sheets

ATTACHMENT OF X-RAY APPARATUS, HIGH TEMPERATURE ATTACHMENT AND X-RAY APPARATUS

BACKGROUND OF THE INVENTION

1. Field of the Invention

The present invention relates to an attachment such as a high temperature attachment arranged around a specimen in an X-ray apparatus and an X-ray apparatus having the attachment.

2. Description of the Related Art

There have been known an X-ray apparatus, which measures X-rays from a specimen when the specimen is irradiated with X-rays from an X-ray source, such as X-rays diffracted by the specimen, by using X-ray detection means such as an X-ray counter. There have been also known An X-ray apparatus, which performs such X-ray measurement by using a specimen housed in an attachment such as a high temperature attachment.

In an X-ray apparatus of such kind, a main role of X-ray detection means is to detect X-rays from a specimen. However, if there are no measures for excluding undesired X-ray from an attachment housing the specimen, the X-ray detection means may also detect the undesired X-rays, causing a result of X-ray detection to be incorrect.

In order to solve such a problem, an X-ray apparatus having a structure such as shown in FIG. 4 has been proposed in which a slit 52 is provided between a specimen S and an X-ray detector 51. In FIG. 4, the specimen S is housed in a temperature regulator 53, which is one of attachments for changing temperature of the specimen S. The slit 52 is constructed with a plurality of walls 54 arranged in parallel along a line shown by an arrow A.

The X-ray detector 51 may comprise a PSPC (Position Sensitive Proportional Counter), which is a one-dimensional X-ray detector. As well known, the PSPC 51 has a lateral slot 56 for receiving X-rays and, when X-rays are incident on any position of the slot 56, outputs a signal corresponding to the position, that is, the diffraction angle of X-ray, and having a level corresponding to an intensity of the X-ray.

In the X-ray apparatus shown in FIG. 4, X-rays radiated from an X-ray source F is collimated by a divergence-limiting slit 57 and directed to the specimen S. When the X-rays incident on the specimen S satisfies the Bragg's diffraction condition with respect to crystal lattice plane of the specimen S, the X-rays are diffracted by the specimen S. The diffracted X-rays pass through the spaces defined by the walls 54 constituting the slit 52 and are incident on the slot 56 of the PSPC 51.

In the above-described conventional X-ray apparatus, when X-rays pass through an X-ray window 59 of the temperature regulator 53, the X-rays are scattered, resulting in scattered X-rays as undesired X-rays. Although the slit 52 is provided for preventing the undesired X-rays from being incident on the X-ray detector 51, the degree of prevention of undesired X-rays is not enough to exclude the effect of undesired X-rays.

SUMMARY OF THE INVENTION

An object of the present invention is to prevent undesired X-rays generated from other locations than a specimen from entering into an X-ray detector.

The inventors of the present invention had conducted various experiments on prevention of undesired X-rays incident on the X-ray detector and have found that it is effective to block undesired X-rays in the vicinity of location at which the undesired X-rays are generated.

(1) In order to achieve the above object, an attachment mounted on a specimen support portion of an X-ray apparatus, according to the present invention, is featured by comprising a cover member covering a specimen and a scattered ray excluding member provided between the cover member and the specimen. The scattered ray excluding member defines a through-hole having an inlet opening having a large area on the side of the cover member and an outlet opening having a small area on the side of the specimen.

According to this attachment, the scattered ray excluding member prevents undesired X-rays from being mixed in travelling paths of X-rays incident on the specimen and diffracted X-rays from the specimen, so that it is possible to perform a highly precise X-ray measurement.

(2) In the above-mentioned attachment, it is preferable that width and height of the inlet opening on the cover member side are larger than those of the outlet opening on the specimen side. Thus, incident angles of the X-rays incident on the specimen in width and height directions can be made large.

(3) In this attachment, the scattered X-ray excluding member may be arranged on the X-ray incident side of the specimen. Thus, it is possible, by the scattered X-ray excluding member, to shield undesired X-rays resulting from scattering of X-rays when the X-rays from an X-ray source pass through the cover member covering the specimen.

(4) In this attachment, the scattered X-ray excluding member can be formed by vertical wail members and lateral wall members. That is, the scattered X-ray excluding member can take in the form of an enclosure having a pair of vertical walls and a pair of lateral walls. With such an enclosure covering a space having square cross section, excludability of scattered X-rays becomes high compared with a scattered X-ray excluding member takes in a dome or semi-cylindrical form.

(5) In this attachment, the cover member may be formed of a visually transparent and X-ray transmitting material and have a semi-spherical form. By forming the cover member of the visually transparent material, it is possible to perform a measurement while watching the specimen. By the employment of the semi-spherical configuration of the cover member, it is easy for a user to handle the cover member.

X-rays diffracted by the specimen impinge to different positions of the inner surface of the cover member according to diffraction angles of X-rays. If the cover member is not in the semi-spherical form, the length of the traveling paths of X-rays within the wall of the cover member are changed according to the impinging positions, resulting in change of absorption of X-rays. This may require taking some steps for compensating the change of absorption of X-rays.

In contrast, since the semi-spherical form is employed in the present invention for the cover member, the length of the traveling paths of X-rays within the wall of the cover member becomes uniform regardless of the impinging positions of X-rays on the inner surface of the cover member. Thus, there is no need to make any compensation.

(6) Further, the attachment mentioned above may have a main body portion to be mounted on the sample support portion of the X-ray apparatus and the cover member can be detachably fixed to the main body portion.

(7) In the attachment having the cover member detachably fixed to the main body portion, the cover member may be mounted on the main body portion by forming a female thread on an inner peripheral surface of the cover member, forming a male thread on an outer peripheral surface of the main body portion and screwing the cover member onto the main body portion. With such construction employed, the cover member can be firmly fixed to the main body portion with a very simple work.

(8) The attachment may further comprise at least one of heater means for heating the specimen, cooling means for cooling the specimen, moisture regulator means for changing moisture condition around the specimen and environment regulation means for setting a gas environment of the specimen different from the atmosphere environment.

The attachment having the heating means constitutes a so-called high temperature attachment and that having the cooling means constitutes a so-called low temperature attachment.

(9) A high temperature attachment to be mounted on a specimen support portion of an X-ray apparatus, according to the present invention, is featured by comprising a specimen table for mounting a specimen thereon, heater means for heating the specimen table, a cover member covering the specimen and a scattered X-ray excluding member provided between the cover member and the specimen. The scattered ray excluding member defines a through-hole having an inlet opening having a large area on the side of the cover member and an outlet opening having a small area on the side of the specimen.

With this high temperature attachment, the scattered ray excluding member prevents undesired X-rays from being mixed in travelling paths of X-rays incident on the specimen and X-rays diffracted by the specimen, so that it is possible to perform highly precise X-ray measurement.

(10) An X-ray apparatus according to the present invention is featured by comprising specimen support means for supporting a specimen, an X-ray source for generating X-rays irradiating the specimen, X-ray detection means for detecting X-rays diffracted by the specimen and an attachment mounted on the specimen support means. The attachment has any one of the constructions mentioned above.

With this X-ray apparatus, the scattered ray excluding member prevents undesired X-rays from being mixed in travelling paths of X-rays incident on the specimen and diffracted X-rays from the specimen, so that it is possible to perform a highly precise X-ray measurement.

(11) In the above-mentioned X-ray apparatus, the X-ray detection means may comprise a two-dimensional X-ray detector. The two-dimensional X-ray detector can detect distribution of X-rays in a plane. That is, it can detect X-rays two-dimensionally. The X-ray detector may be a dry X-ray plate, an X-ray film or a plane storage phosphor. Alternatively, the X-ray detector may comprise a CCD (Charge Coupled Device) sensor including two-dimensionally arranged CCDs.

The dry X-ray plate is a flat X-ray detection element composed of a base substrate formed of a relatively hard material and having a suitable area and an emulsion film containing silver halide as a main constituent and painted on one of or both surfaces of the base substrate. By developing an exposed dry X-ray plate, a two-dimensional distribution of X-ray can be obtained on the surface of the dry X-ray plate.

The X-ray film is a flat X-ray detection element composed of a thin, flexible plastic film and an emulsion film containing silver halide as a main constituent and painted on one of or both surfaces of the base plate. By developing an exposed X-ray film, a two-dimensional distribution of X-ray can be obtained on the surface of the X-ray film.

The X-ray detector comprising the plane storage phosphor is an energy storage type radiation-detecting element. The storage phosphor is formed by painting a surface of a flexible film or a flat plate type film, etc., with storage fluorescent material such as, for example, $BaFBr:Er^{2+}$ fine crystals. The storage phosphor can store X-ray, etc., in the form of energy and can discharge the energy externally as light by irradiating it with stimulation pumping light such as laser light.

That is, when the storage phosphor is irradiated with X-rays, an image of X-ray is stored in the storage phosphor as a latent image of energy and, when the storage type fluorescent material is irradiated with stimulation pumping light such as laser light, the energy is discharged externally as light. By detecting the light by photoelectric tube, etc., diffraction angle and intensity of the X-ray contributed to the formation of the latent image can be measured. Sensitivity of the storage phosphor is about 10 to 60 times that of the conventional X-ray film and has a wide dynamic range from $10^6$ to $10^8$.

The plane type CCD sensor includes a plurality of CCDs arranged two-dimensionally on an X-ray receiving surface. The CCD sensor includes an electrode array formed by linearly or two-dimensionally arranging a plurality of electrodes on an insulating film formed on, for example, a silicon substrate, the electrode array being arranged correspondingly to a X-ray receiving slot of the X-ray detector.

When portions of the CCD sensor corresponding to the respective electrodes of the electrode array thereof are irradiated with X-ray, electric charges are stored below the electrodes and the electric charges are transferred externally by sequentially applying a voltage between the electrodes and the substrate.

In the X-ray apparatus using the two-dimensional X-ray detector, two-dimensionally dispersed X-rays are detected simultaneously and, therefore, possibility of detecting undesired X-rays becomes high. However, when the scattered ray excluding member of the present invention is used, it is possible to reliably prevent an exposure of the two-dimensional X-ray detector with undesired X-rays.

DETAILED DESCRIPTION OF THE PREFERRED EMBODIMENTS

Figure 1:
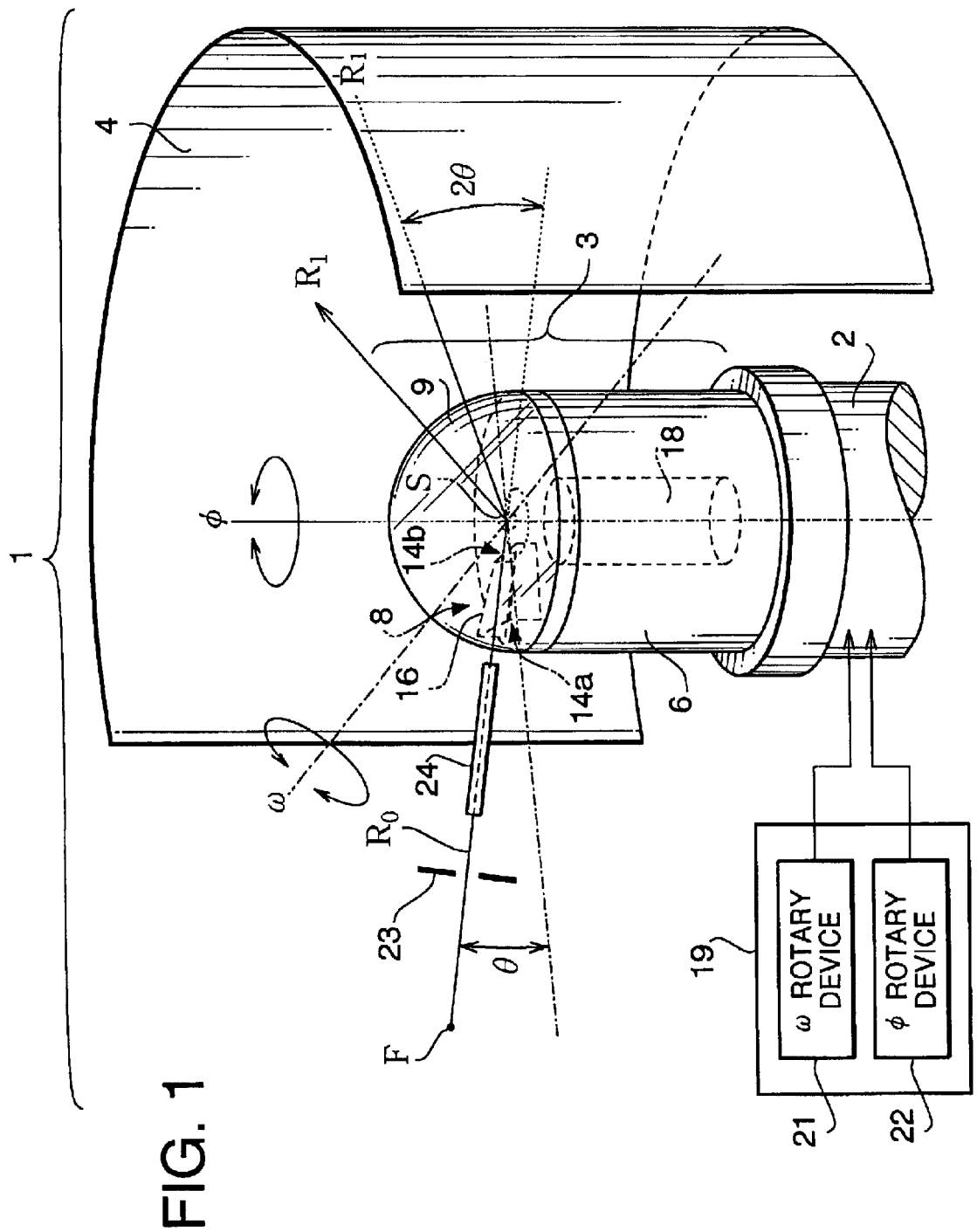
FIG. 1 is a perspective view of an embodiment of an attachment, a high temperature attachment and an X-ray apparatus, respectively, according to of the present invention.

FIG. 1 shows an embodiment of an X-ray apparatus and an attachment according to the present invention, respectively. The attachment shown in FIG. 1 is a high temperature attachment. An X-ray apparatus 1 includes an X-ray source F radiating X-rays, a support member 2 for supporting a specimen S, a high temperature attachment 3 fixedly mounted on the support member 2 and an X-ray detector 4 for detecting X-rays diffracted by the specimen S.

The X-ray detector 4 is constructed as a two-dimensional X-ray detector having a storage phosphor provided on an X-ray receiving surface thereof. The X-ray detector 4 has an inside surface of the storage phosphor concaved with the specimen S being a center of curvature thereof. The X-ray source F may be constructed with a filament (not shown), which emits thermoelectrons when heated, and a target (not shown) arranged in an opposing relation to the filament.

Figure 2:
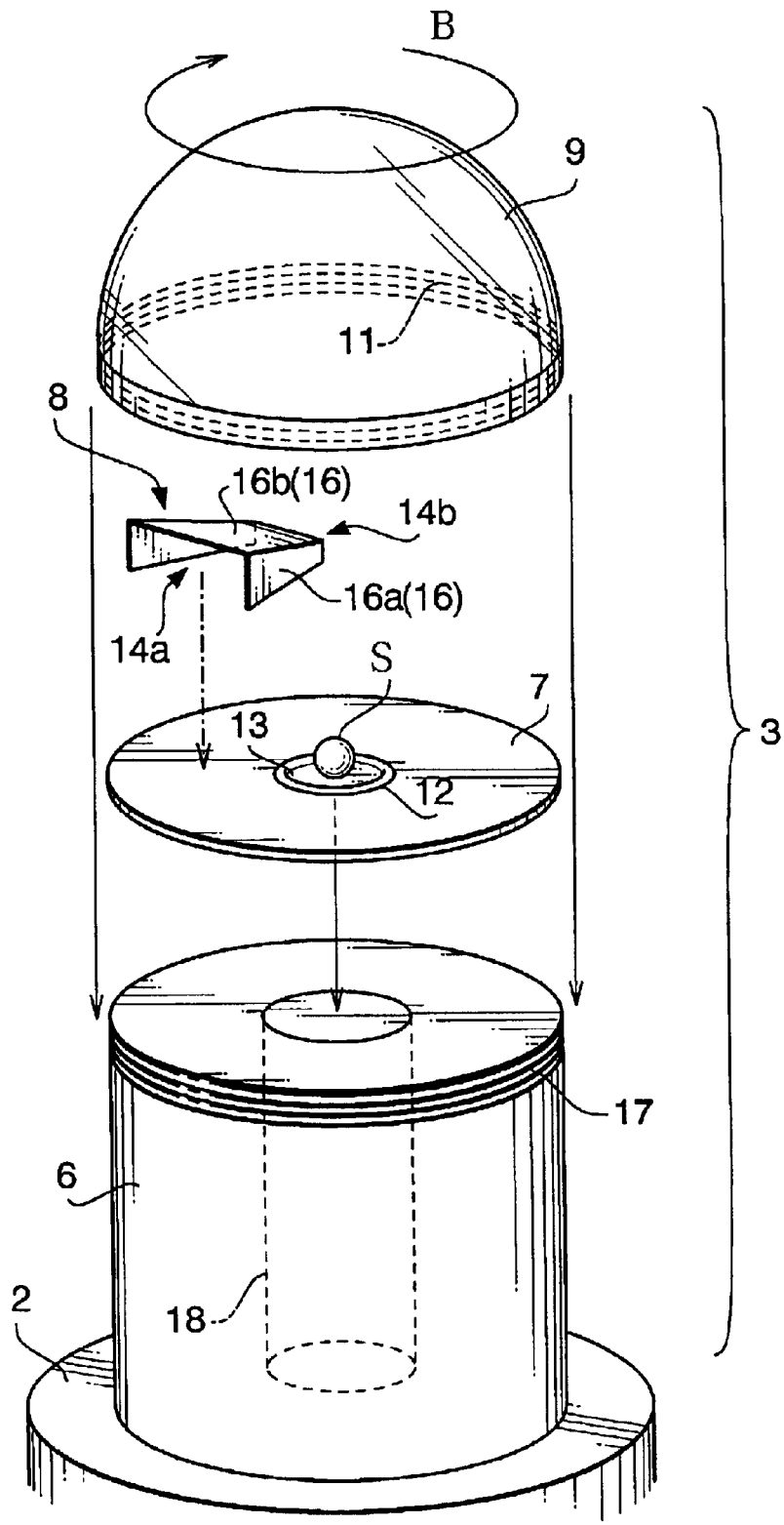
FIG. 2 is a disassembled perspective view of a high temperature attachment shown in FIG. 1.

The high temperature attachment 3 includes, as shown in FIG. 2, a main body portion 6 fixed to the specimen support member 2 by suitable fixing means such as screws or an adhesive, a specimen table 7 mounted on an upper end portion of the main body portion 6, a scattered ray excluding member 8 fixed on an upper surface of the specimen table 7 and a cover member 9 fitted on an upper end portion of the main body portion 6.

The cover member 9 is formed of a visually transparent and X-ray transmitting material such as a plastic material and has a semi-sphere configuration. An inner peripheral surface of a lower portion of the cover member 9 is threaded to form a female thread 11 and an outer peripheral surface of an upper end portion of the main body portion 6 is threaded to form a male thread 17. By putting the cover member 9 on the main body portion 6 and rotating the cover member 9 in an arrow B, the cover member 9 can be fixed to the upper portion of the main body portion 6.

The specimen table 7 is a circular disk formed of a suitable material such as stainless steal and has a specimen-mounting portion 13 partitioned in a center of the circular disk by an annular protrusion 12. The specimen S to be measured is mounted on the specimen-mounting portion 13. The specimen table 7 is fixedly in contact with the upper end portion of the main body portion 6 when the cover member 9 is fixed to the main body portion 6.

The scattered ray excluding member 8 may be formed by bending a wall plate 16 of a metal material such as stainless steal, which does not transmit X-rays, to form a large inlet opening 14a on the side of the cover member 9 and a small outlet opening 14b on the side of the specimen S. In this embodiment, the scattered ray excluding member 8 takes in the form of a box, case or enclosure having square or rectangular cross section, which is provided by bending the wall plate 16 to form longitudinal wall portions 16a and a lateral wall portion 16b. Further, the scattered ray excluding member 8 is fixed to the upper surface of the specimen table 7 or to an inner surface of the cover member 9 by screws or an adhesive.

Figure 3A:
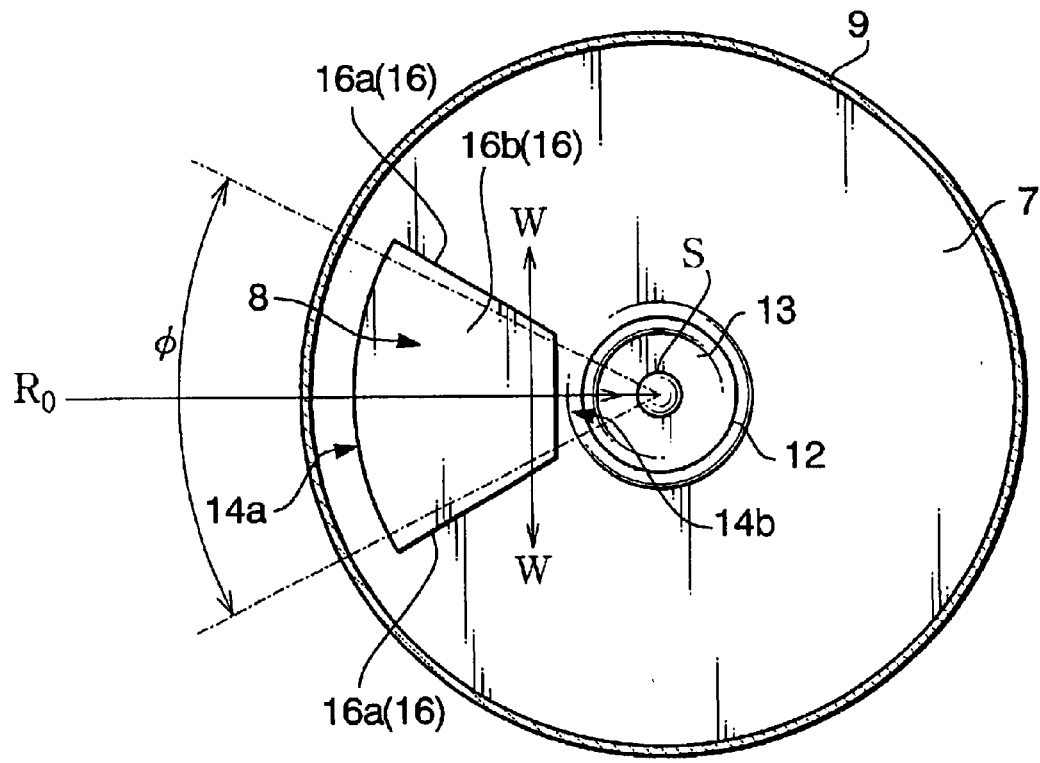
FIG. 3(a) is a partially cross-sectioned plan view of a main portion of the high temperature attachment shown in FIG. 2.
Figure 3B:
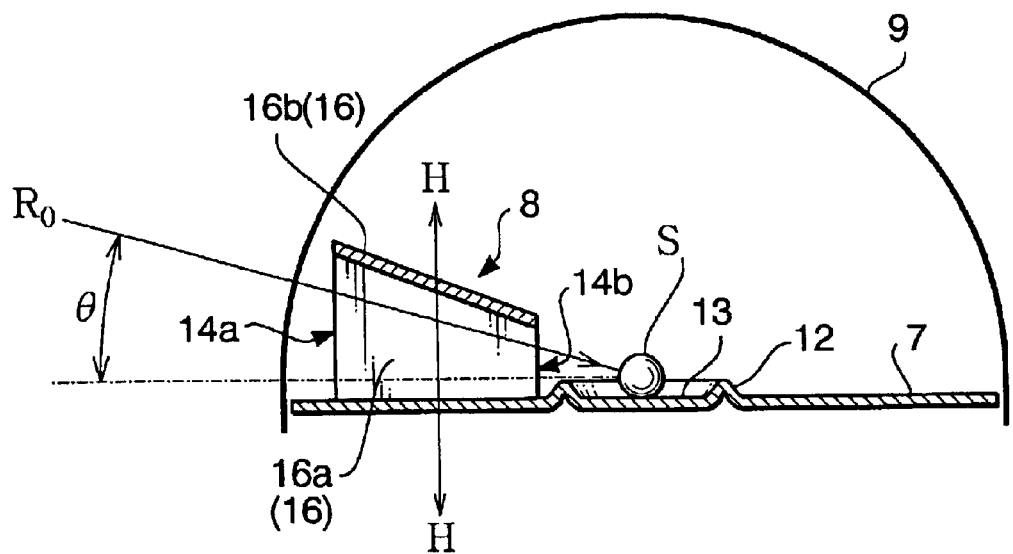
FIG. 3(b) is a cross sectional side view of the main portion of the high temperature attachment shown in FIG. 2.
Figure 4:
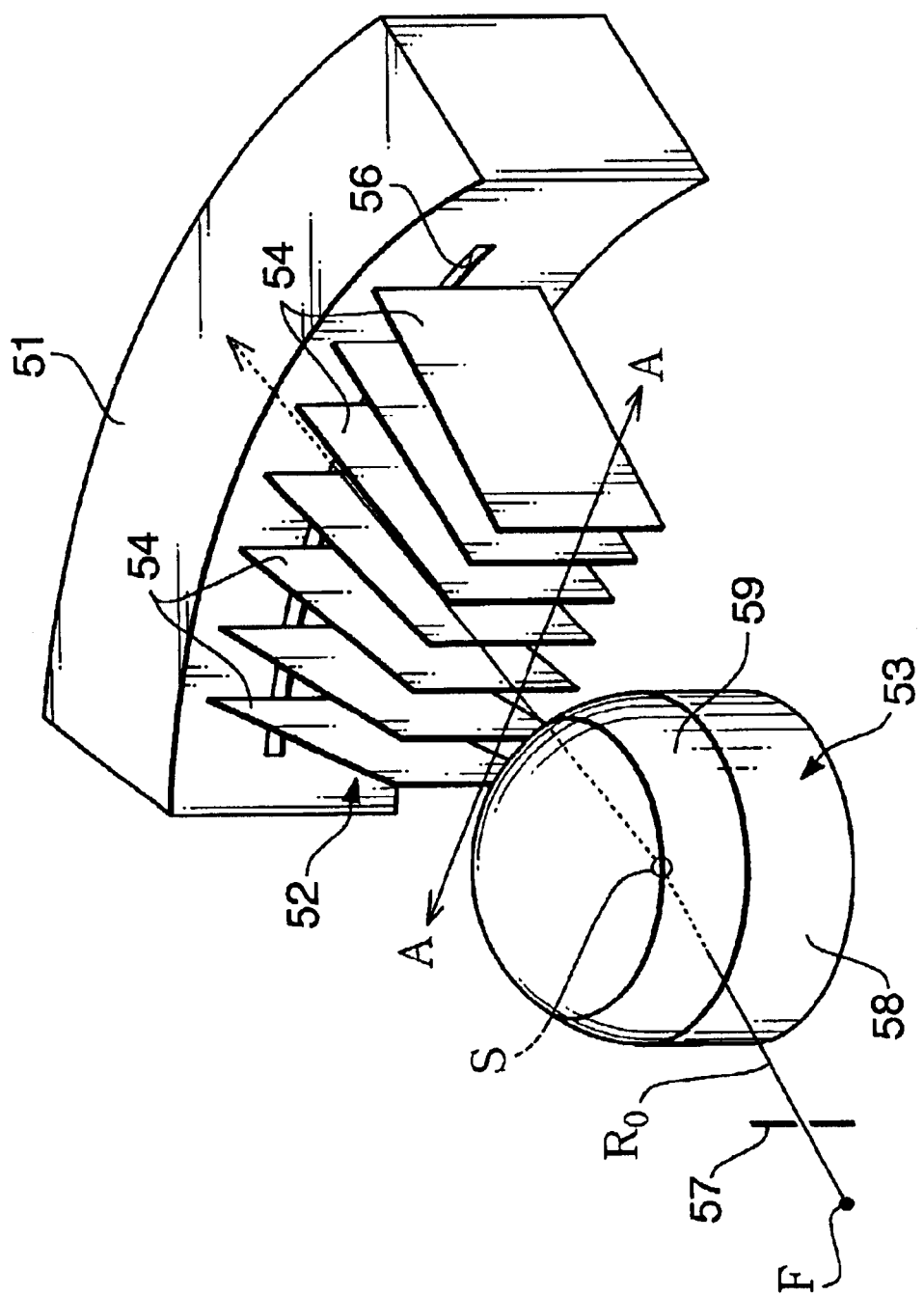
FIG. 4 is a perspective view of an example of a conventional X-ray apparatus.

As shown in FIG. 3(a) and FIG. 3(b), the scattered ray excluding member 8 is arranged on the side of the specimen S on which X-ray R0 is incident, that is, the X-ray incident side of the specimen S. Further, width W and height H of the inlet opening 14a of the scattered ray excluding member 8 on the side of the cover member 9 are larger than those of the outlet opening 14b thereof on the side of the specimen S, respectively. The size of the inlet opening 14a in the width direction W is larger than a predetermined in-surface rotation angle φ in the X-ray measurement and the size of the inlet opening 14a in the height direction H is larger than a predetermined X-ray incident angle θ in the X-ray measurement.

In FIG. 2, the main body portion 6 is cylindrical and a rod-like heater 18 is provided within the cylindrical main body portion 6. A heat-generating member such as a coil is housed in the rod-like heater 18 in such a way that heat is radiated from an upper surface thereof. When a current is supplied to the heat-generating member within the rod-like heater 18, the heat-generating member generates heat. The heat thus generated is transmitted through the upper end surface of the main body portion 6 to the specimen table 7 to heat the specimen S on the table 7 to a high temperature.

Controller (not shown) controls an amount of current supplied to the heat-generating member of the rod-like heater 18 on the basis of a predetermined program, such that the temperature of the specimen S is changed according to the program. Incidentally, in order to change the temperature of the specimen S correctly, cooling means such as a cooling fin (not shown) may be provided around the rod-like heater 18.

In FIG. 1, the support member 2 for supporting the high temperature attachment 3 is driven by an angle-measuring device, that is, a goniometer 19. The goniometer 19 includes a ω rotary device 21 and a φ rotary device 22. The ω rotary device 21 rotates the high temperature attachment 3, and hence, the specimen S, about a ω axis extending perpendicularly to an optical path of the incident X-ray R0. With this rotation of the specimen S, it is possible to change the incident angle θ of the X-ray R0 incident on the specimen S.

The φ rotary device 22 rotates the high temperature attachment 3, and hence, the specimen S, about a φ axis line extending through the specimen S perpendicularly to the ω axis line. By this in-plane rotation of the specimen S, it is possible to change orientation of crystal lattice plane within the specimen S with respect to the incident X-ray R0.

The ω rotary device 21 and the φ rotary device 22 may have arbitrary structures, respectively. For example, each of the rotary devices may be constructed with a power source such as a pulse motor capable of precisely controlling its rotation angle and power transmission means for transmitting rotation of the power source to the support member 2. The power transmission means may be a power transmission mechanism constructed with a worm gear and a worm wheel.

An operation of the X-ray apparatus having the above-mentioned construction will be described. In FIG. 2, the cover member 9 is removed from the main body portion 6 of the high temperature attachment 3 fixed to the support member 2 of the X-ray apparatus to expose the specimen table 7 and a specimen S to be measured is mounted on the exposed specimen table 7. Then, the cover member 9 is fixed to the main body portion 6 again.

Thereafter, the ω rotary device 21 is activated to set the incident angle φ of the incident X-ray R0 with respect to the specimen S to a value inherent to the specimen S, and then a current is supplied to the rod-like heater 18 to generate heat and temperature of the specimen S is controlled to make it higher or lower or to maintain it at a constant value, according to the predetermined program.

When the temperature of the specimen S becomes the predetermined value, the X-ray source F is activated to radiate X-rays. A portion of the X-rays from the X-ray source F is selected by a divergence-limiting slit 23 to be directed to the specimen S. The X-ray portion is further collimated to a parallel X-ray beam having a small cross sectional area by a collimator 24 on demand.

The collimated X-ray portion from the collimator 24 passes through the cover member 9 and the scattered ray excluding member 8 to the specimen S. When the X-ray R0 incident on the specimen S and the crystal lattice plane of the specimen S satisfy the Bragg's diffraction condition, the X-ray R0 is diffracted by the specimen S. The diffracted X-ray R0 travels at a diffraction angle 2θ and reaches the two-dimensional X-ray detector 4 to expose the storage phosphor surface thereof.

With such exposure, an exposed image pattern inherent to the specimen S is stored in the storage phosphor of the two-dimensional X-ray detector 4 as a latent image of energy. The X-ray detector 4 having the latent image of energy is removed from the X-ray apparatus 1 and mounted on a predetermined read position of an X-ray image reader (not shown) in which the latent image is read out. In concrete, a whole surface of the storage phosphor is scanned with stimulation pumping light such as laser light and light discharged from the storage phosphor during the scanning is detected by a photoelectric converter (not shown). Thereafter, the diffraction angle of X-ray contributed to the formation of the latent image held on the storage phosphor of the X-ray detector 4 and intensity thereof are obtained by calculation on the basis of a result of the detection.

In FIG. 1, when the specimen S is irradiated with the X-ray R0, the X-ray R0 passes through the cover member 9. During the passage of the X-ray R0 through a portion of the cover member 9, a portion of the X-rays is scattered by the portion of the cover member 9. The scattered X-rays are undesired X-rays in view of the measurement of the diffracted X-rays from the specimen S. A component of the scattered X-rays, which travels toward the X-ray detector 4, is blocked by the wall 16 of the scattered ray excluding member 8, so that it does not reach the X-ray detector 4.

If the scattered X-ray reaches the X-ray detector 4, the exposed image would be formed in portion having no relation to the diffracted X-ray R1 from the specimen S. Therefore, the measurement may become incorrect. Further, since, in such case, a wide area of the X-ray detector 4 may be exposed by the scattered X-rays and background components in a result of measurement become high, fine exposure data to be measured may be hidden by the background components.

In the present invention, however, the scattered X-rays travelling from the cover member 9 toward the X-ray detector 4 can be blocked by the scattered ray excluding member 8 and so it is possible to perform a highly precise X-ray measurement by the X-ray detector 4.

Incidentally, as shown in FIG. 3(a) and FIG. 3(b), width W and height H of the inlet opening 14a defined by the walls 16 constituting the scattered ray excluding member 8 and positioned on the side of the cover member 9 are larger than those of the outlet opening 14b thereof on the side of the specimen S, respectively. Therefore, it is possible to completely block the scattered X-rays from the portion of the cover member 9 through which X-rays pass. Further, since the size of the inlet opening 14a is larger as mentioned above, it is possible to set the in-surface rotation angle φ and the incident angle θ of the incident X-ray R0 to large values, respectively.

The X-rays scattered by the specimen S on the incident side thereof may expose a wide area of the X-ray detector 4. In the present invention, however, the scattered ray excluding member 8 arranged on the X-ray incident side of the specimen S can block the scattered X-rays in the vicinity of a source thereof. Therefore, the excludability of scattered X-rays is very high.

The scattered X-ray excluding member 8 of the present invention takes in the form of the box constructed with the vertical wall portions 16a and the lateral wall portions 16b. Therefore, shielding efficiency of scattered X-ray is very high compared with the scattered X-ray excluding member 8 taking in the form of semi-cylinder. Further, since the cover member 9 is formed of a visually transparent plastic material, it is possible for an operator to confirm the specimen S under X-ray measurement visually.

Further, since the semi-spherical cover member 9 of the high temperature attachment 3 is detachably mounted on the main body portion 6, it is possible to perform a mounting or a demounting operation of the specimen S with respect to the specimen table 7 very easily.

Although the present invention has been described with reference to the preferred embodiments, the present invention is not limited thereto and various modifications of the embodiments can be done by those skilled in the art within the scope of the present invention defined by the appended claims.

For example, although, in the embodiment shown in FIG. 1, the attachment has been described as the high temperature attachment 3 having the heating means for heating the specimen, the present invention can be equally applied to a low temperature attachment having cooling means, an attachment having moisture regulation means for changing moisture around a specimen or an attachment having environment regulation means for providing an environment of other gas than atmospheric gas around a specimen, etc. These attachments commonly have cover members surrounding specimens.

Further, although the two-dimensional X-ray detector having a light receiving surface constructed with a two-dimensional storage phosphor is used in the embodiment shown in FIG. 1, a dry X-ray plate, an X-ray film or a two-dimensional CCD detector may be used in lieu of the detector having the storage phosphor.

As described hereinbefore, according to the attachment of the present invention for use in an X-ray apparatus, it is possible to prevent undesired X-rays from entering into paths of X-rays incident on the specimen and exiting from the specimen. Therefore, undesired X-rays never enter into the X-ray detector together with the aimed X-rays, making the highly precise X-ray measurement possible.

What is claimed is:

1. An attachment mounted on a specimen support portion of an X-ray apparatus, comprising
   a cover member surrounding a specimen and
   a scattered ray excluding member provided between said cover member and said specimen,
   said scattered ray excluding member defining a through-hole having an inlet opening having a large area on the side of said cover member and an outlet opening having a small area on the side of said specimen.

2. An attachment as claimed in claim 1, wherein width and height of said inlet opening on the side of said cover member are larger than those of said outlet opening on the side of said specimen.

3. An attachment as claimed in claim 2, wherein said scattered X-ray excluding member is arranged on the incident side of X-rays with respect to said specimen.

4. An attachment as claimed in claim 3, wherein said scattered X-ray excluding member is formed by longitudinal walls and lateral walls perpendicular to said longitudinal walls.

5. An attachment as claimed in claim 4, wherein said cover member is formed of a visually transparent and X-ray transmitting material and have a semi-spherical form.

6. An attachment as claimed in claim 5, further comprising a main body portion mounted on said specimen support portion of said X-ray apparatus, wherein said cover member is detachably fixed to said main body portion.

7. An attachment as claimed in claim 6, wherein said cover member has an inner peripheral surface formed with a female thread, said main body portion has an outer peripheral surface formed with a male thread and said cover member is mounted on said main body portion by screwing said cover member onto said main body portion by using said male and female threads.

8. An attachment as claimed in claim 7, further comprising at least one of heater means for heating said specimen, cooling means for cooling said specimen, moisture regulator means for changing moisture around said specimen and environment regulation means for setting an environment of said specimen in a gas environment different from atmosphere.

9. An X-ray apparatus including;
specimen support means for supporting a specimen,
an X-ray source for generating X-rays irradiating said specimen,
X-ray detection means for detecting X-rays generated by said specimen, and
an attachment mounted on said specimen support means, said attachment having a construction defined in claim 2.

10. An attachment as claimed in claim 1, wherein said scattered X-ray excluding member is arranged on the incident side of X-rays with respect to said specimen.

11. An X-ray apparatus including;
specimen support means for supporting a specimen,
an X-ray source for generating X-rays irradiating said specimen,
X-ray detection means for detecting X-rays generated by said specimen, and
an attachment mounted on said specimen support means, said attachment having a construction defined in claim 10.

12. An attachment as claimed in claim 1, wherein said scattered X-ray excluding member is formed by longitudinal walls and lateral walls perpendicular to said longitudinal walls.

13. An X-ray apparatus including;
specimen support means for supporting a specimen,
an X-ray source for generating X-rays irradiating said specimen,
X-ray detection means for detecting X-rays generated by said specimen, and
an attachment mounted on said specimen support means, said attachment having a construction defined in claim 12.

14. An attachment as claimed in claim 1, wherein said cover member is formed of a visually transparent and X-ray transmitting material and have a semi-spherical form.

15. An X-ray apparatus including;
specimen support means for supporting a specimen,
an X-ray source for generating X-rays irradiating said specimen,
X-ray detection means for detecting X-rays generated by said specimen, and
an attachment mounted on said specimen support means, said attachment having a construction defined in claim 14.

16. An attachment as claimed in claim 1, further comprising a main body portion mounted on said specimen support portion of said X-ray apparatus, wherein said cover member is detachably fixed to said main body portion.

17. An attachment as claimed in claim 16, wherein said cover member has an inner peripheral surface formed with a female thread, said main body portion has an outer peripheral surface formed with a male thread and said cover member is mounted on said main body portion by screwing said cover member onto said main body portion by using said male and female threads.

18. An X-ray apparatus including;
specimen support means for supporting a specimen,
an X-ray source for generating X-rays irradiating said specimen,
X-ray detection means for detecting X-rays generated by said specimen, and
an attachment mounted on said specimen support means, said attachment having a construction defined in claim 17.

19. An X-ray apparatus including;
specimen support means for supporting a specimen,
an X-ray source for generating X-rays irradiating said specimen,
X-ray detection means for detecting X-rays generated by said specimen, and
an attachment mounted on said specimen support means, said attachment having a construction defined in claim 16.

20. An attachment as claimed in claim 1, further comprising at least one of heater means for heating said specimen, cooling means for cooling said specimen, moisture regulator means for changing moisture around said specimen and environment regulation means for setting an environment of said specimen in a gas environment different from atmosphere.

21. An X-ray apparatus including;
specimen support means for supporting a specimen,
an X-ray source for generating X-rays irradiating said specimen,
X-ray detection means for detecting X-rays generated by said specimen, and
an attachment mounted on said specimen support means, said attachment having a construction defined in claim 20.

22. An X-ray apparatus including;
specimen support means for supporting a specimen,
an X-ray source for generating X-rays irradiating said specimen,
X-ray detection means for detecting X-rays generated by said specimen, and
an attachment mounted on said specimen support means, said attachment having a construction defined in claim 1.

23. An X-ray apparatus as claimed in claim 22, wherein said X-ray detection means includes a two-dimensional X-ray detector.

24. A high temperature attachment mounted on a specimen support portion of an X-ray apparatus, comprising;
a specimen table for mounting a specimen thereon,
heater means for heating said specimen table,
a cover member covering said specimen, and
a scattered X-ray excluding member provided between said cover member and said specimen,
said scattered ray excluding member defining a through-hole having an opening having a large area on the side of said cover member and an opening having a small area on the side of said specimen.

* * * * *